United States Patent [19]

Greenough et al.

[11] Patent Number: 4,994,626
[45] Date of Patent: Feb. 19, 1991

[54] METHOD FOR THE PREPARATION OF METHYL ETHERS OF POLYETHER POLYOLS EMPLOYING DIMETHYLSULFATE AS A METHYLATING AGENT

[75] Inventors: Ronald E. Greenough, Southgate; Jay G. Otten, Flat Rock, both of Mich.; Stefan Birnbach, Ludwigshafen; Jochen Houben, Worms, both of Fed. Rep. of Germany

[73] Assignee: BASF Corporation, Parsippany, N.J.

[21] Appl. No.: 433,133

[22] Filed: Nov. 8, 1989

[51] Int. Cl.$^5$ .............................................. C07C 41/01
[52] U.S. Cl. .................................. 568/618; 568/619; 568/616; 568/609; 568/608; 568/606; 568/613
[58] Field of Search ............... 568/618, 619, 616, 609, 568/608, 606, 613

[56] References Cited

U.S. PATENT DOCUMENTS 4,922,029  5/1990  Birnbach et al. .................. 568/619

FOREIGN PATENT DOCUMENTS 0302487  2/1989  European Pat. Off. ............ 568/618

Primary Examiner—Howard T. Mars
Attorney, Agent, or Firm—Rupert B. Hurley; Michael R. Chipaloski

[57] ABSTRACT

A process for preparing an etherified polyoxyalkylene derivative of the formula

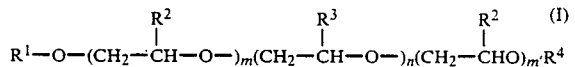

$$R^1-O-(CH_2-CH-O-)_m(CH_2-CH-O-)_n(CH_2-CHO)_{m'}R^4 \quad (I)$$

with substituents $R^2$, $R^3$, $R^2$ on the respective CH groups wherein $R^1$ and $R^4$ are identical or different and are each independently $C_1$–$C_{20}$ alkyl, $C_3$–$C_5$ alkenyl, $C_6$–$C_{20}$ aryl, $C_6$–$C_{20}$ alkyl aryl, $C_6$–$C_{20}$ cycloalkyl, and mixtures thereof, $R^2$ and $R^3$ are identical or different and independent of each other are H, $CH_3$, $CH_3CH_2$, and mixtures thereof, m, m' and n are identical or different and are each greater than or equal to zero, with the proviso that $m+m'+n$ is from 3 to 300; by reacting a polyoxyalkylene compound of the formula.

5 Claims, No Drawings

METHOD FOR THE PREPARATION OF METHYL ETHERS OF POLYETHER POLYOLS EMPLOYING DIMETHYLSULFATE AS A METHYLATING AGENT

BACKGROUND OF THE INVENTION

1. Field of the Invention

The present invention relates to an improved process for the preparation of etherified polyoxyalkylene derivatives by reacting the corresponding free hydroxy compound with a dialkyl sulfate in the presence of an aqueous solution of an alkali metal hydroxide. More specifically, the present invention is directed to an improved method for preparing methyl ethers of polyether polyol employing dimethylsulfate as a methylating agent.

2. Description of the Prior Art

It is known that polyoxyalkylene compounds having one or more terminal hydroxyl groups can be etherified by first converting the free hydroxy compound with an alkali metal, an alcoholate, a hydride or a hydroxide of an alkali metal into the corresponding alkali metal alcoholate and then further reacting the alcoholate with an alkylating agent, such as, dialkyl sulfate or an alkyl halide.

German Patent Application No. 2 800 710 discloses a process for the preparation of etherified polyoxyalkylene compounds in which the free hydroxy compound is treated with an organic halide, such as butyl chloride in the presence of an aqueous solution of sodium hydroxide or potassium hydroxide whose initial concentration is of sodium or potassium hydroxide is not less than 30 percent by weight. The process of the German disclosure is carried out at a temperature of from about 80°-100° C.

European Patent No. 302487 discloses a process for the preparation of etherified polyoxyalkylene derivatives by reacting the corresponding free hydroxy compound with a dialkyl sulfate in the presence of an aqueous solution of an alkali metal hydroxide. The reference describes a two-step process where it is essential to add reactants in a two-step process to form the etherified polyoxyalkylene derivative. The present invention relates to a single step process wherein improved yields and substantial savings in time and costs are realized.

East German Patent No. 244 549 discloses a process for etherification of oligoglycol monochlorides which is characterized by the fact that the oligoglycol chlorides are reacted with dialkyl sulfates in the presence of an inorganic base at temperatures usual for alkylation reactions. The ethers produced are useful for pharmaceutically active substance, surfactants and pesticides.

Hay, U.S. Pat. No. 3,402,144, discloses a process to metalate polyphenylene ethers with alkali metal alkyls or aryls to give activated alkali metal-containing polymers. These metalated polymers readily react with chemical reagents to produce modified polymers, and also react with anionically polymerizable monomers to produce graft copolymers.

Leverett, U.S. Pat. No. 3,393,179, discloses a process for the preparation of a high molecular weight polyoxymethylene alkyl ether which consists of contacting the unetherified polymer with a combination of dimethyl or diethyl sulfate and an orthoester in a process which does not require the addition of a base or acid to catalyze the reaction. The reaction temperature is in the range of 100° C. to 180° C. and preferably is carried out in an inert hydrocarbon medium.

SUMMARY OF THE INVENTION

The present invention relates to an improved process for the preparation of methyl ethers of polyethers employing dimethyl sulfate as the methylating agent. The process is carried out under ambient temperatures of 35° C. or less and involves adding all the sodium hydroxide metalating agent at the beginning of the reaction and gradually adding dimethyl sulfate (DMS) over a period of time to give optimal capping of the polyethers. This can result in a substantial savings of dimethyl sulfate and/or improved capping efficiency. Further, the present invention is operated at low temperatures, whereas the processes of the prior art operate at elevated temperatures. It was unexpected to find that keeping the reaction temperature below 35° C. along with adding all of the NaOH prior to adding the DMS, results in significant improvements in capping efficiency.

DETAILED DESCRIPTION OF THE PREFERRED EMBODIMENTS

The present invention is concerned with an improved method of preparing alkyl, aryl, or alkaryl ethers of polyethers employing dialkyl, diaryl, or dialkaryl sulfate as the methylating agent.

The present invention is concerned with the preparation of polyoxyalkylene derivatives of the formula:

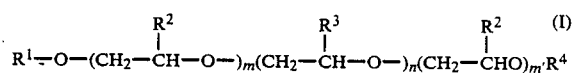

wherein $R^1$ and $R^4$ are identical or different and are each independently a $C_1$-$C_{20}$ alkyl, $C_3$-$C_5$ alkenyl, $C_6$-$C_{20}$ aryl, $C_6$-$C_{20}$ alkyl, aryl, $C_6$-$C_{20}$ cycloalkyl, and mixture thereof, $R^2$ and $R^3$ are identical or different and independently of each other are each hydrogen, methyl or ethyl, and mixtures thereof, and m, m' and n are identical or different and are each greater than or equal to 0, with the proviso that the sum of $m+m'+n$ is from 3 to 300.

The polyoxyalkylene derivative of formula I is prepared by reacting a polyoxyalkylene compound of the following formula:

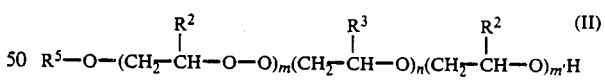

wherein $R^5$ is hydrogen, $C_1$-$C_{20}$-alkyl, $C_3$-$C_5$-alkenyl, $C_6$-$C_{20}$ aryl, $C_{6-C20}$ alkyl aryl, $C_{6-C20}$ cycloalkyl groups, and mixtures thereof, and $R^2$, $R^3$, m, m' and n each have the above defined meanings. The polyoxyalkylene compound of formula II is reacted with a dialkyl, diaryl, dialkylaryl, or cycloalkyl sulfate of the following formula:

where $R^4$ has the above meaning. The polyoxyalkylene compound of Formula II is reacted with the sulfate of Formula III in the presence of an aqueous solution of an alkali metal hydroxide at a reaction temperature of from about 20 to 35° C., and not less than one mole of alkali metal hydroxide is used per mole equivalent of organic hydroxyl groups.

Those skilled in the art recognize that all of the alkyl groups in the above-described Formulas I, II, and III may be either straight-chain or branched.

$R^1$, $R^4$ and $R^5$ may be selected from the group consisting of methyl, ethyl, propyl, isopropyl, butyl, isobutyl, or sec-butyl. In addition, $R^1$ and $R^5$ can further be selected from the group consisting of pentyl, isopentyl, neopentyl, tert-pentyl, hexyl, 2-methyl-pentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl, tetradecyl, pentadecyl, hexadecyl, heptadecyl, octadecyl, nonadecyl, eicosyl, allyl or methallyl and mixtures thereof. Preferably, in Formula II, $R^5$ is hydrogen or a $C_8$–$C_{16}$ alkyl group. Other preferred polyoxyalkylene derivatives of Formula II are those in which the sum of m, m' and n is from 3 to 300 or preferably from 5 to 100.

The preferred alkylating agent is a dialkyl sulfate of Formula III where $R^4$ is ethyl or most preferably, methyl. If polyoxyalkylene derivatives of Formula II where $R^5$ is hydrogen are used as the starting materials, dietherification occurs. In the case of dietherification, etherified polyoxyalkylene derivatives of Formula I where $R^1$ is identical to $R^4$ are obtained.

The alkali metal hydroxides which are suitable for use in the present invention may be selected from the group consisting of lithium hydroxide, potassium hydroxide, sodium hydroxide and mixtures thereof. In the most preferred embodiment, sodium hydroxide aqueous solution is preferred. This process is useful in capping oxyalkylated block copolymers and heteric copolymers, oxyalkylated alcohols, oxyalkylated alkylphenols including other initiators such as amines, polyamines, glycerine, trimethylolpropane, pentaerythritol, sugars and related polyhydroxy aromatics, phenolic resins and any other suitable active hydrogen baring compound whose oxyalkylates are not hydrolizable under the conditions described herein, polyethylene glycols, polypropylene glycols, and alcohols. The reaction scheme of the present invention may be depicted as follows:

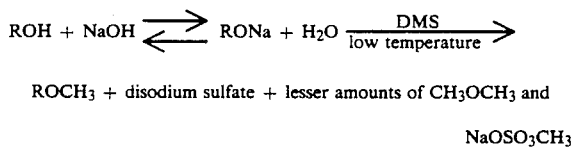

$ROCH_3$ + disodium sulfate + lesser amounts of $CH_3OCH_3$ and $NaOSO_3CH_3$

The following examples are offered to illustrate various aspects of the invention. Those skilled in the art recognize that they are not to be construed as limiting the scope and spirit of the invention.

| DIMETHYL-CAPPED POLYOL: SYNTHETIC PROCEDURE "A" (PRIOR ART EXAMPLE) | |
|---|---|
| CHARGES: | |
| (1) EOxPOyEOx copolymer, ca. 13 wt. % EO, molecular weight ca. 1900 | 491.3 gm |
| (2) 50% SODIUM HYDROXIDE | 220.0 gm |
| (3) DIMETHYL SULFATE, 99+ % | 27.7 gm |
| (4) 50% SODIUM HYDROXIDE | 220.0 gm |
| (5) DIMETHYL SULFATE | 46.2 gm |
| (6) DIMETHYL SULFATE | 17.4 gm |
| (7) TAP WATER | 650.0 gm |

PROCEDURE

To a two-liter four-necked round-bottom flask fit with stirrer, thermometer, nitrogen inlet and outlet, and two pressure-equalized addition funnels (100 ml and 250 ml volumes) are charged the polyether (1) and the first NaOH charge (2). The vessel is purged with nitrogen, and a slight stream is maintained for the duration of the synthesis. Agitation is begun, and the first dimethyl sulfate charge (3) is added via addition funnel over a period of twenty minutes. This is followed by the concurrent addition (from separate addition funnels) over a fifty-minute period of the second 50% NaOH and dimethyl sulfate charges (4 and 5). The third DMS charge (6) is then added over a period of fifteen minutes. Optionally, the exotherm of the reaction may be moderated by partially submerging the reaction vessel in a cold water or ice-water bath during the dimethyl sulfate additions.

The mixture is then reacted out for a minimum of 80 minutes, followed by the addition of the water (7). Stirring is continued for a minimum of 30 minutes. Stirring is terminated and the contents of the vessel are transferred to a separatory funnel. The mixture is allowed to stand undisturbed. Within seconds, the water and organic layers begin to separate, and the water layer is drained. Approximately thirty to sixty minutes are allowed for the separation.

The crude product is transferred to a round-bottom flask and is treated with magnesium silicate adsorbent (ca. 3% by weight), followed by stripping at <1 mm Hg and 105 C for 2.5 hours. The stripped material is then filtered through #4 Whatman paper to yield the final product. The percent capping of the product is determined from its hydroxyl number. An alternative treatment of the crude product is the neutralization of the residual NaOH with phosphoric acid (the charge being determined via titration of the alkali in the crude product), followed by stripping in like manner, with optional filtration.

| DIMETHYL-CAPPED POLYOL: SYNTHETIC PROCEDURE "B" (PRESENT INVENTION) | |
|---|---|
| CHARGES: | |
| 1. EOxPOyEOx copolymer, ca. 13 wt. % EO, molecular weight ca. 1900 | 491.3 gm |
| 2. 50% SODIUM HYDROXIDE | 440.0 gm |
| 3. DIMETHYL SULFATE, 99+ % | 91.3 gm |
| 4. TAP WATER | 650.0 gm |

PROCEDURE

To a two-liter four-necked round-bottom flask fit with stirrer, thermometer, nitrogen inlet and outlet, and two pressure-equalized addition funnels (100 ml and 250 ml volumes) are charged the polyether (1) and the NaOH charge (2). The vessel is purged with nitrogen, and a slight stream is maintained for the duration of the synthesis. Agitation is begun, and the dimethyl sulfate charge 3) is added slowly via addition funnel over a period of about ninety minutes. Optionally, the exotherm of the reaction may be moderated by partially submerging the reaction vessel in a cold water or ice-water bath during the dimethyl sulfate addition. The highest degree of capping will be obtained when such cooling is employed.

The mixture is then allowed to react out for about 2.5 hours, followed by the addition of the water (4). Stirring is continued for a minimum of 30 minutes. Stirring is terminated and the contents of the vessel are transferred to a separatory funnel. The mixture is allowed to stand undisturbed. Within seconds, the water and organic layers begin to separate, and the water layer is drained. Approximately thirty to sixty minutes are allowed for the separation.

The crude product is transferred to a round-bottom flask and is treated with magnesium silicate adsorbent (ca. 3% by weight), followed by stripping at <1 mm Hg and 105° C. for 2.5 hours. The stripped material is then filtered through #4 Whatman paper to yield the final product. The percent capping of the product is determined from its hydroxyl number. An alternative treatment of the crude product is the neutralization of the residual NaOH with phosphoric acid or some other mineral or organic acid the charge being determined via titration of the alkali in the crude product), followed by stripping in like manner, with optional filtration.

In Table I, which follows, Examples 1 and 2 are preparations employing the prior art Procedure "A", without and with auxiliary cooling, respectively. Examples 3 and 4 employ the present invention Procedure "B", without and with cooling, respectively. Examples 5, 6, and 7 follow modifications of Procedure B"; 5 and 6 employ a rapid DMS addition with and without cooling, respectively, while 7 uses 20 % less dimethyl sulfate (with cooling). Example 7 shows that, when all of the sodium hydroxide is added to the polyether at the beginning, reduced levels of DMS still provide for very high capping efficiency. Example 8 can be considered to be a modification of Procedure "A" employing shorter caustic and DMS addition times.

wherein $R^1$ and $R^4$ are identical or different and are each independently $C_1$-$C_{20}$ alkyl, $C_3$-$C_5$ alkenyl, $C_6$-$C_{20}$ aryl, $C_6$-$C_{20}$ alkyl aryl, $C_6$-$C_{20}$ cycloalkyl, and mixtures thereof, $R^2$ and $R^3$ are identical or different and independent of each other are H, $CH_3$, $CH_3CH_2$, and mixtures thereof, m, m' and n are identical or different and are each greater than or equal to zero, with the proviso that m+m'+n is from 3 to 300; by reacting a polyoxyalkylene compound of the formula

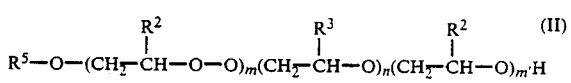

wherein $R^5$ is hydrogen, $C_1$-$C_{20}$ alkyl, $C_3$-$C_5$ alkenyl, $C_6$-$C_{20}$ aryl, $C_6$-$C_{20}$ alkyl aryl, $C_6$-$C_{20}$ cycloalkyl, and mixtures thereof; $R^2$, $R^3$, m, m' and n are as defined above, with a dialkyl, diaryl, dialkylaryl, dicycloalkyl sulfate, and mixtures thereof, of the formula $$(R^4O)_2SO_2, \quad (III)$$

wherein $R^4$ is as defined above, in the presence of an aqueous solution of an alkali metal hydroxide at a temperature less than about 35° C., and using not less than one mole of alkali metal hydroxide per mole equivalent of organic hydroxyl groups, wherein all the alkali metal hydroxide is added at once before the addition of the sulfate of formula III.

2. The process of claim 1, wherein $R^1$ and $R^4$ and $R^5$ are selected from the group consisting of methyl, ethyl, propyl, isopropyl, butyl, isobutyl, or sec-butyl.

3. The process of claim 1, wherein $R^1$ and $R^5$ are selected from the group consisting of pentyl, isopentyl, neopentyl, tert-pentyl, hexyl, 2-methyl-pentyl, heptyl,

TABLE I

| Example | Addition (min.)* 50% NaOH | Times DMS | Temperatures °C. Avg. | Min. | Max. | % Capping | Description (Procedure/ Modifications) |
|---|---|---|---|---|---|---|---|
| 1 | 50** | 85 | 56 | 24 | 78 | 86.6 | "A" without cooling |
| 2 | 55** | 90 | 26 | 22 | 33 | 93.5 | "A" with cooling |
| 3 | 0 | 85 | 38 | 26 | 52 | 90.8 | "B" without cooling |
| 4 | 0 | 85 | 25 | 22 | 25 | 97.6 | "B" with cooling |
| 5 | 0 | 7 | 30 | 20 | 39 | 92.5 | "B", Rapid Dimethyl Sulfate Addition with cooling |
| 6 | 0 | 7 | 64 | 28 | 80 | 85.7 | "B", Rapid Dimethyl Sulfate Addition, without cooling |
| 7 | 0 | 65*** | 26 | 23 | 29 | 94.9 | "B" employing 20% less Dimethyl Sulfate, with cooling |
| 8 | 24** | 41 | 40 | 32 | 43 | 86.5 | "A" employing shorter addition times for both the 50% Sodium Hydroxide and the Dimethyl Sulfate |

*A "0" in an addition time column indicates that this reagent was mixed with the polyether, and the other reagent added over the specified period of time.
**In Examples 1, 2, and 8, half of the caustic charge was added at the beginning along with the polyether, and the other half added concurrently with the second DMS charge over the specified period of time.
***The dimethyl sulfate charge was reduced by 20% for Example 7.

The embodiments of the invention in which an exclusive privilege or property is claimed are defined as follows:

1. A process for preparing an etherified polyoxyalkylene derivative of the formula

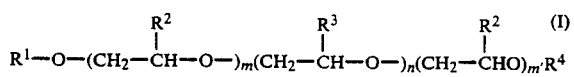

octyl, 2-ethylhexyl, isooctyl, nonyl, isononyl, decyl, isodecyl, undecyl, dodecyl, tridecyl, 3,5,5,7-tetramethylnonyl, isotridecyl, tetradecyl, pentadecyl, hexadecyl, heptadecyl, octadecyl, nonadecyl, eicosyl, allyl or methallyl and mixtures thereof.

4. The process of claim 1, wherein $R^5$ is hydrogen or a $C_8$-$C_{18}$ alkyl group.

5. The process of claim 1, wherein $R^4$ is selected from the group consisting of methyl, ethyl and mixtures thereof.

* * * * *